United States Patent [19]

Zampini

[11] Plant 4,038

[45] Apr. 12, 1977

[54] FLOWERING CRAB APPLE TREE

[75] Inventor: James W. Zampini, Perry, Ohio

[73] Assignee: Lake County Nursery Exchange, Inc., Perry, Ohio

[21] Appl. No.: 678,538

[22] Filed: Apr. 20, 1976

[51] Int. Cl.[2] ..... A01H 5/03

[52] U.S. Cl. ..... Plt./34

[58] Field of Search ..... Plt./34

*Primary Examiner*—Robert E. Bagwill

*Attorney, Agent, or Firm*—Teare, Teare & Sammon

EXEMPLARY CLAIM

1. A new and distinct variety of flowering Malus crab apple tree, substantially as herein shown and described, characterized particularly by an upright, semi-dwarf growth habit, an arching and weeping effect of the branches, attractive pinkish colored flowers and abundant bright dark red colored fruits that may hang all winter, and which has apparent resistance to diseases which are common to most Malus species.

3 Drawing Figures

The present invention relates to the new and distinct variety of crab apple tree, which was discovered by me as a newly found seedling on my cultivated property, at Perry, Ohio. More particularly, the present invention relates to a novel variety of Malus, flowering crab apple, having unusual and distinctive characteristics, now available as the "Weeping Candied Apple" Trademark tree of Lake County Nursery Exchange, Inc. Perry, Ohio.

My new flowering crab apple tree has a "weeping" form with most of the branches extending generally parallel to the ground, and then gently descending toward their ends on a slight arcuate angle toward the ground. The tree may be characterized as a semi-dwarf tree showing much vigor in its early years of growth. In the invention, a mature tree forming a flattened canopy may have an estimated mature height of approximately 12 feet.

The definite parentage of my new crab apple seedling is unknown, but the texture of the leaf is thicker and firmer than the Hopa. The leaf color is dark green with an overcast of a darker wine color (as compared to the Hopa) on the top side, and with the under side being green with an overcast of silver. The trunk and branches of the trees are smooth and of light purplish to dark burgundy color toward the stems.

The blossoms are of a fairly large size of a dark pink color which cover the stems in profusion. The flowering is especially good as the flowers appear before the stems are covered by the leaves.

The fruit is of a bright, dark red, having an approximate ⅜ inch transverse diameter. The fruit is much smaller and holds longer and is firmer and brighter, as compared to the Hopa. The fruit color is held late into the season with the firm fruit still on the tree in December. Unlike most crab apple trees, the fruit does not drop when mature, but dries on the tree and becomes forage food for winter birds, for example.

The crab apple tree of the present invention exhibits vigorous and hardy habits of growth, particularly in the early years. This variety evidences resistance to insects and diseases which are common to most Malus species, including applescab, blight, and mildew.

The accompanying drawings show typical specimens of the flowers, foliage, branches and fruit of my new crab apple variety as depicted in color as nearly true as it is reasonably possible to make the same in a photographic illustration of this character.

Referring now more particularly to the drawings.

Figure 1:
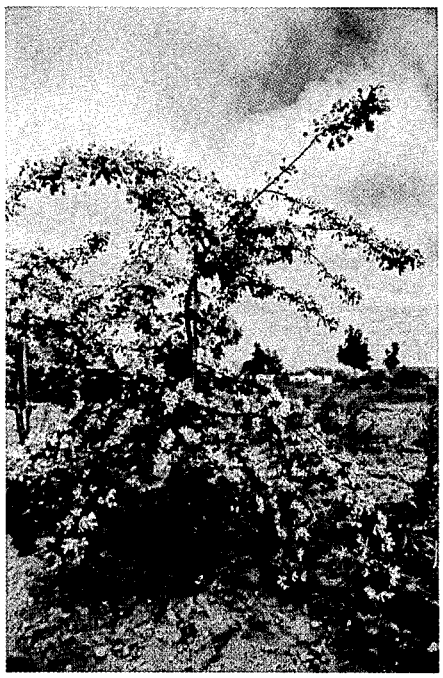
FIG. 1 shows my new flower crab apple tree in the spring blooming season.
Figure 2:
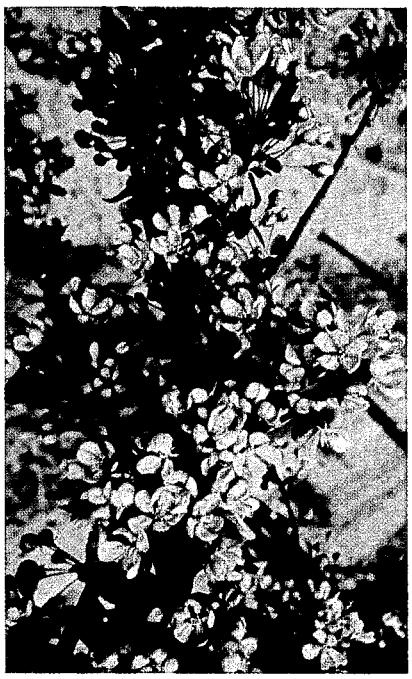
FIG. 2 shows a branchlet of such tree bearing a number of open flowers.
Figure 3:
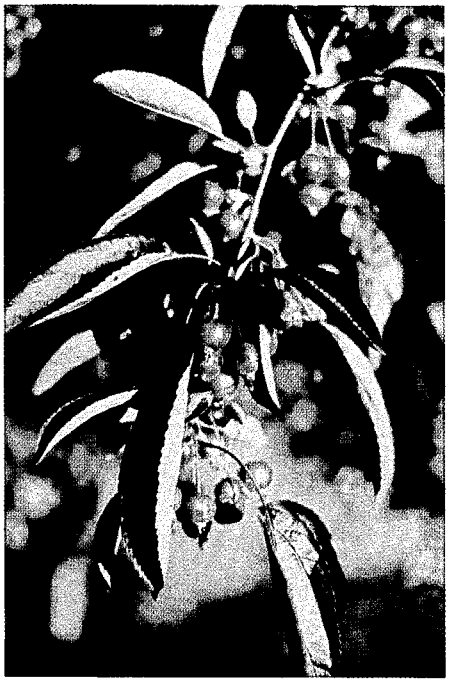
FIG. 3 shows a branchlet of such tree illustrating the fruit and leaves thereof.

Asexual reproduction of my new flowering crab apple variety was performed by me by budding at Perry, Ohio, Zone 5. Such reproduction illustrates the foregoing characteristics and distinctions take place and are established and transmitted through succeeding propogations of the tree. The following is a specific description by way of specific example of such new variety, color terminology being in reference to the Munsell Book of Color 1950, hereinafter referred to as "Munsell".

From observations made in respect to specimens grown at Perry, Ohio: Fruit will hang all winter.

Tree: Maturity to a height about 12 feet; vigorous, upright, but having an arching and "weeping" effect; rapid growing, particularly in early years; and productive and regular bearer.

Leaves: Medium size about 3 inches long and about 1¾ inches wide; having ovate shape and being substantially smooth.

Color: Green (Munsell 7.5 GY 3/4).

Flowers: Medium size; date of first bloom being about May 1; date of full bloom being about 3 to 5 days later; color being reddish pink (Munsell 10 RP 9/1), changing to deep whitish pink (Munsell 10 RP 7/8).

Fruit: Having generally uniform transverse diameter of about 3/8 inches being of a generally oblong-ovoid shape; color being bright dark red (Munsell SR 5/14).

I claim:

1. A new and distinct variety of flowering Malus crab apple tree, substantially as herein shown and described, characterized particularly by an upright, semi-dwarf growth habit, an arching and weeping effect of the branches, attractive pinkish colored flowers and abundant bright dark red colored fruits that may hang all winter, and which has apparent resistance to diseases which are common to most Malus species.

* * * * *

UNITED STATES PATENT AND TRADEMARK OFFICE

CERTIFICATE OF CORRECTION

PATENT NO. : PP 4,038

DATED : April 12, 1977

INVENTOR(S) : James W. Zampini

It is certified that error appears in the above-identified patent and that said Letters Patent is hereby corrected as shown below:

Column 1, line 7, change "Weeping Candied Apple" to --Weepcanzam-- and delete the term "Trademark".

Signed and Sealed this

Twenty-eighth Day of May, 1991

*Attest:*

HARRY F. MANBECK, JR.

*Attesting Officer*

*Commissioner of Patents and Trademarks*